(12) United States Patent
Burckhardt

(10) Patent No.: US 6,439,715 B2
(45) Date of Patent: Aug. 27, 2002

(54) MAGNIFYING GLASS WITH ILLUMINATION MEANS FOR USE IN MEDICINE AND AN ILLUMINATION MEANS

(76) Inventor: Rainer Burckhardt, Muehlweg 49, 92637 Weiden (DE)

(*) Notice: Subject to any disclaimer, the term of this patent is extended or adjusted under 35 U.S.C. 154(b) by 0 days.

(21) Appl. No.: 09/863,426

(22) Filed: May 24, 2001

(30) Foreign Application Priority Data

| Jun. 9, 2000 | (DE) | 100 28 264 |
| Jun. 16, 2000 | (DE) | 100 29 707 |
| Jun. 29, 2000 | (DE) | 100 31 685 |

(51) Int. Cl.[7] ................................................. G02C 7/08
(52) U.S. Cl. ................................................................ 351/57
(58) Field of Search ........................... 351/59, 55, 130, 351/155, 156; 600/160, 181; 250/559.29

(56) References Cited

U.S. PATENT DOCUMENTS

| 5,345,087 A | * | 9/1994 | Luber et al. ........... 250/559.29 |
| 5,841,509 A |  | 11/1998 | Harooni et al. |
| 6,110,106 A | * | 8/2000 | MacKinnon et al. ........ 600/181 |

FOREIGN PATENT DOCUMENTS

DE    WO 96/25873    8/1996

* cited by examiner

*Primary Examiner*—George Manuel
(74) *Attorney, Agent, or Firm*—Hoffman, Wasson & Gitler, PC

(57) ABSTRACT

A novel magnifying glass for use in medicine, with magnifying glass optics which can be attached to a carrier element on the head of the user. At least one illumination means is provided on the magnifying glass, with an electrically operated light source.

22 Claims, 5 Drawing Sheets

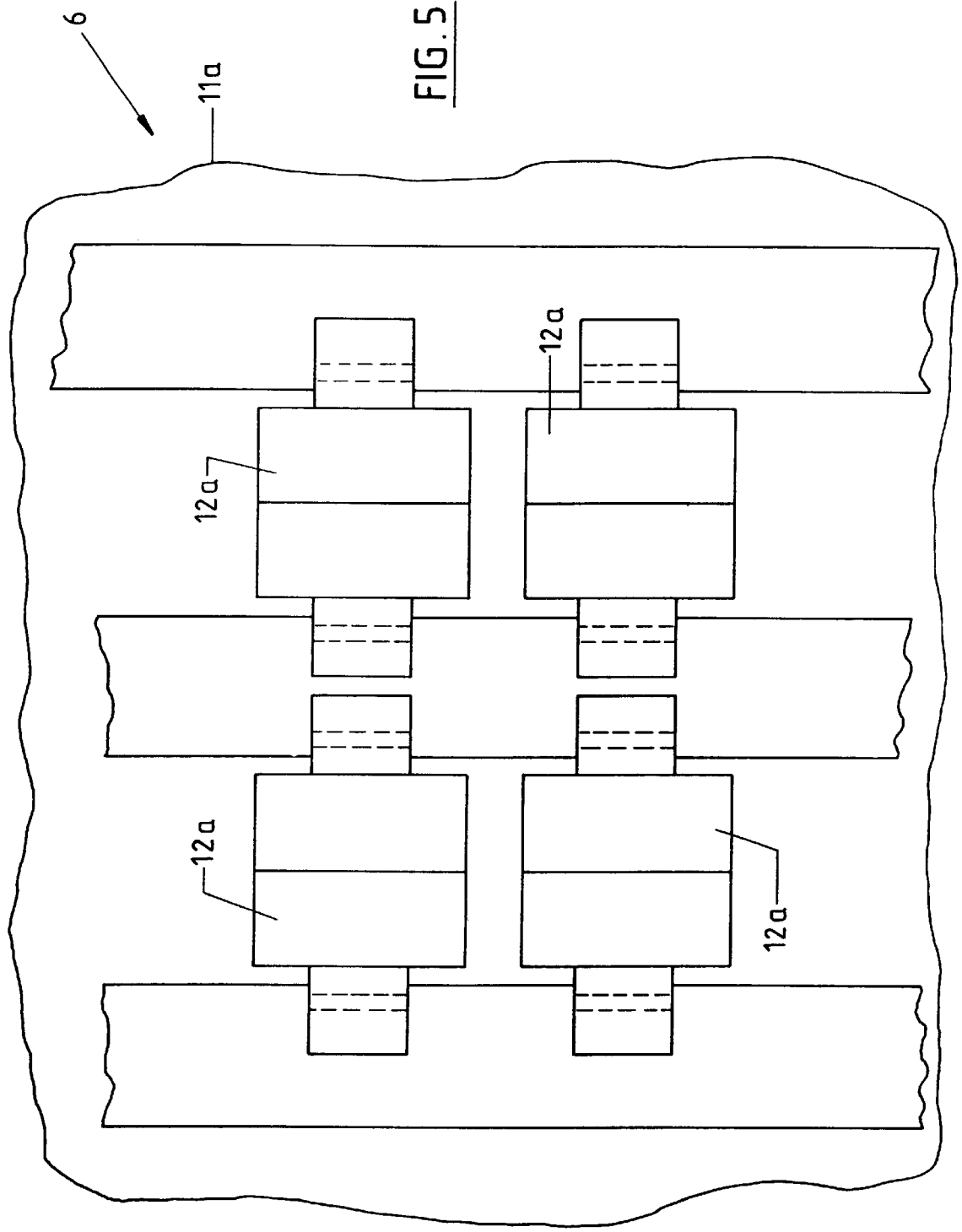

MAGNIFYING GLASS WITH ILLUMINATION MEANS FOR USE IN MEDICINE AND AN ILLUMINATION MEANS

BACKGROUND OF THE INVENTION

The invention relates to a magnifying glass and to an illumination means.

Especially in medicine, for example in microsurgery, but also in other areas of medicine, magnifying glasses are known. These include telescopic spectacles or magnifying glasses mounted on a headband. Furthermore, illumination means are also known for these magnifying glasses, with which the respective viewing field or surgical field can be illuminated.

Light sources for these illumination means have recently been halogen lamps with the pertinent optics. The major disadvantages of these illumination means include high heat evolution, relatively large dimensions, and high electric power requirements for their operation so that either only stationary power supply devices with no mobility or battery-operated power supply units which can be carried on the body and are heavy can be used.

In particular, a binocular magnifying glass which can be worn with a headband with two magnifying optics and one illumination means (WO 96/25873) is known. It consists of a light source spatially separate from the magnifying glass and the illumination means there. The light from which source is coupled into the illumination means via an optical fiber. This known version has the problem that the optical fiber is disruptive when a binocular magnifying glass is being used and the freedom of movement of the user is adversely affected.

Furthermore, a binocular ophthalmoscope for viewing the retina of the human eye is also known (U.S. Pat. No. 5,841,509). To illuminate the retina there is a light source such as a light emitting diode, with light mixed into the beam path of the ophthalmoscope so that the illumination of the retina to be examined takes place by part of the optics of the ophthalmoscope. The light source is housed either directly in the housing of the ophthalmoscope or separate from it, the light in turn then being coupled via an optical fiber. To avoid damage to the retina, the light source has only very low power. This device is neither designed nor suited as a magnifying glass for viewing the working field or the surgical field.

The object of the invention is to avoid the problems of the prior art. To achieve this object, the magnifying glass is made and the illumination means is utilized.

SUMMARY OF THE INVENTION

One special feature of the invention is that the light source is formed by several LEDs with a high illumination intensity of at least 2000 mcd, for example with an illumination intensity of at least 3000 mcd. The light of the individual LEDs is focused at the focus by the focusing element which is assigned to the respective LED. The LEDs are supplied with power via a portable power supply unit located separately from the light source and connected to it via a power supply cable.

In one especially advantageous embodiment of the invention, there is an actuating element separate from the illumination means controlling the illumination means by contact or by proximity, especially turning it on and off. This is especially important in surgical applications with respect to hygiene and sterility to be maintained.

BRIEF DESCRIPTION OF THE INVENTION

The invention is detailed below using the figures on one embodiment.

FIG. 5 shows another embodiment of the illumination means for use in the magnifying glass of FIGS. 1 and 2.

DETAILED DESCRIPTION OF THE INVENTION

Figure 1:
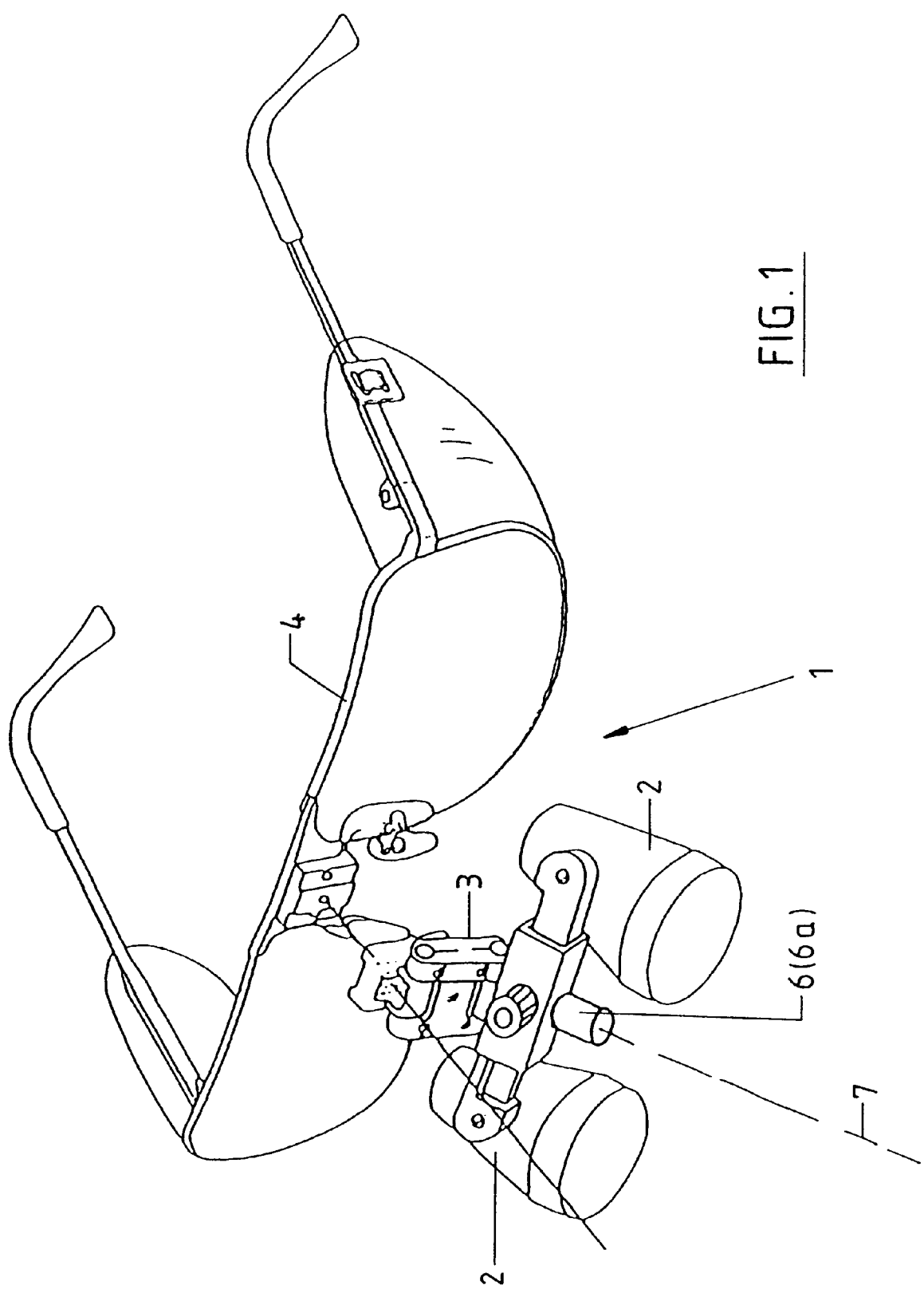
FIG. 1 shows one embodiment of the magnifying glass as telescopic spectacles.

In the figures a surgical microscope or a magnifying glass with double optics is especially, but not exclusively, suited for use in medicine, for example dentistry, microsurgery, etc.

The two optics 2 are conventionally provided on an adjustable adapter 3. The magnifying glass 1 can be selectively attached to spectacles 4 or to eyeglass frames to form telescopic spectacles or to another holder which is attached to the head of the user, for example to a headband.

Between the two optics 2 on the adapter 3 is an illumination means 6 delivering a combined light beam 7 illuminating the area viewed through the magnifying glass 1 or through the optics 2 (for example, surgical or viewing area).

Figure 2:
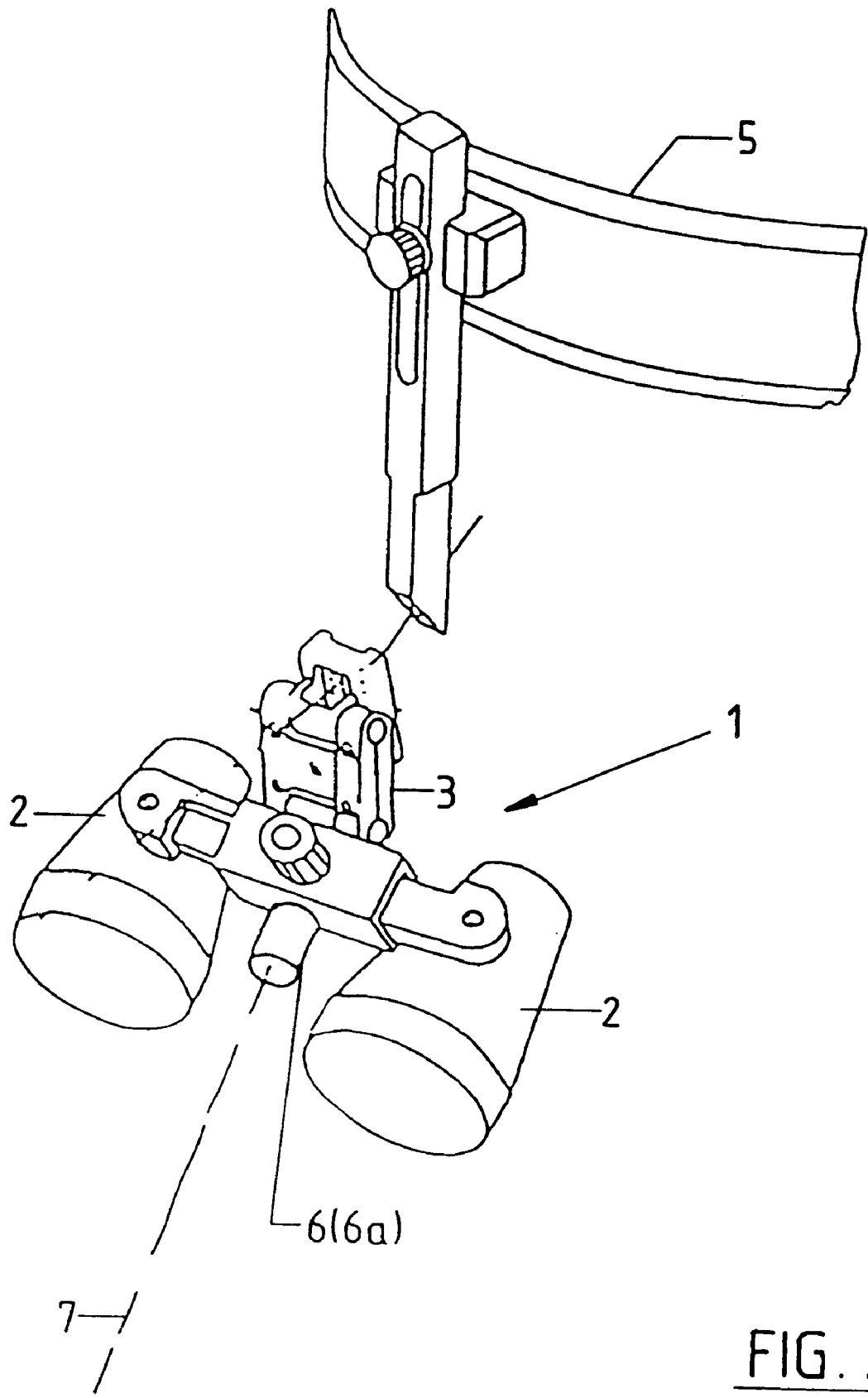
FIG. 2 shows another embodiment of the magnifying glass for attachment to a headband.
Figure 3:
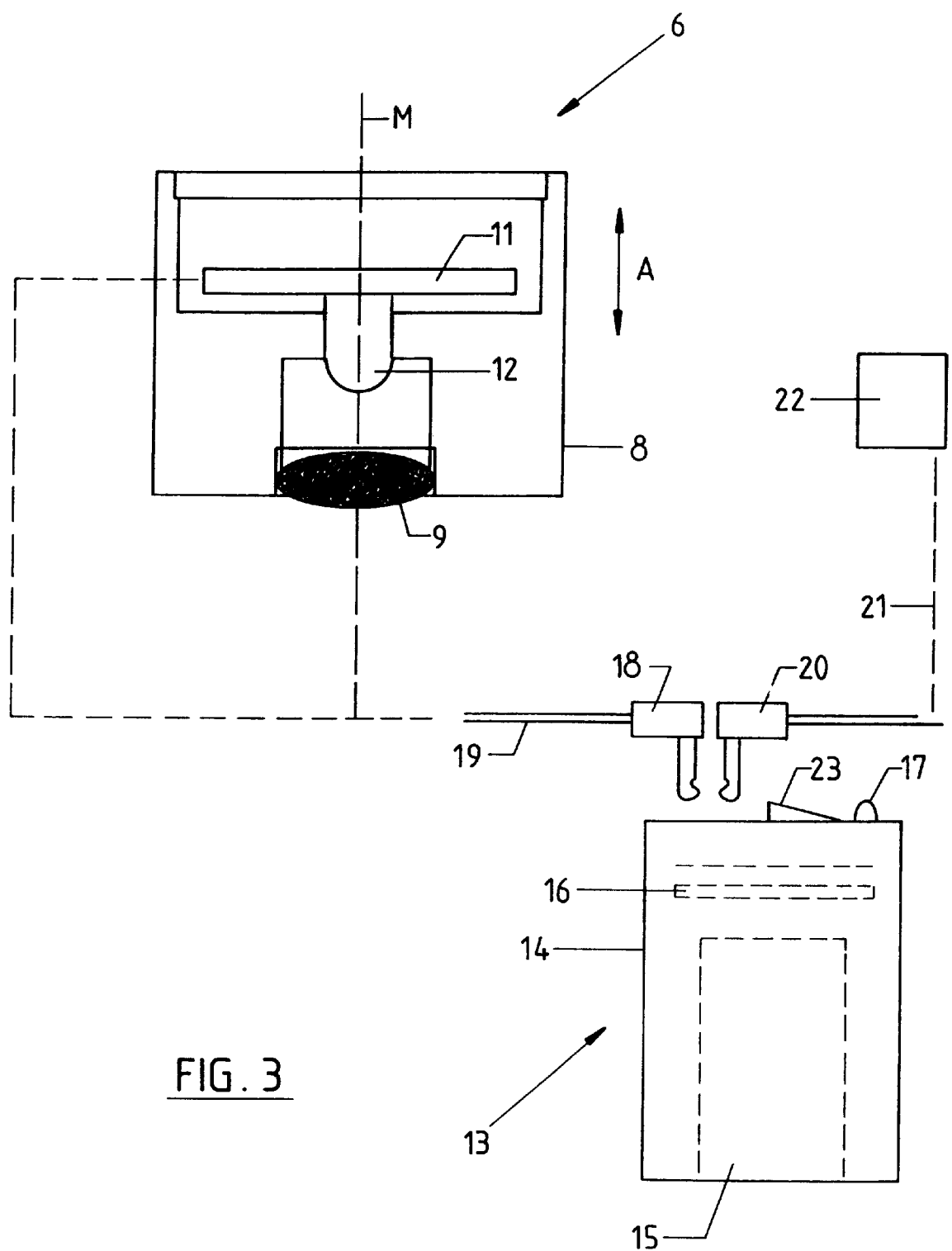
FIG. 3 shows a simplified section through the illumination means for use in the magnifying glass of FIGS. 1 and 2.

FIG. 2 shows the illumination means 6 in detail. It consists essentially of a cylindrical housing 8 having on the front side an arrangement of several lenses. The embodiment shown has a total of three lenses 9 forming focusing optics and are arranged uniformly offset around the center axis M of the housing 8 in a common plane perpendicular to this center axis. Within the housing 8 is a board 11 with its surface sides perpendicular to the center plane M and which on its side facing the lens arrangement 10 has several LEDs 12. The number of LEDs in the embodiment shown is equal to the number of lenses 9 and each LED being located coaxially or essentially coaxially to the optical axis of a lens 9.

The LEDs used are so-called "ultra-bright LEDs", i.e. light emitting diodes having especially high efficiency, for example, an efficiency of 85% and thus at low electrical power consumption ensuring high light output and have a light spectrum which corresponds to that of white light, i.e. for example daylight or approximately daylight.

Other advantages of the illumination means 6 are, among others:

Due to the high efficiency of the LEDs used, the illumination means 6 has only low heat evolution. It can therefore be positioned with the magnifying glass closely in the area of the eyes and the nose of the user.

Furthermore, at any time there is the possibility of focusing and adjusting the illumination means 6 by hand without the prior need to turn off and cool the illumination means 6.

The illumination means 6 can be produced with extremely small dimensions and with very low weight. This enables optimum positioning of the illumination means 6 on the magnifying glass 1 and comfortable wearing of the magnifying glass 1, for example, on eyeglass frames 4 or on a headband 5, since the total weight of the magnifying glass 1.

Illumination means 6 is not noticeably influenced by the illumination means 6.

By attaching the illumination means 6 to the magnifying glass 1 the light beam 7 is automatically entrained when the user of the magnifying glass 1 moves his head so that the viewing field is always optimally illuminated.

As is indicated in FIG. 2 with the double arrow A, the board 11 with the LEDs can be adjusted in the direction of the center axis M relative to the lens arrangement 10 for focusing or imaging the individual light beams at the focus in the viewing plane. There is also the possibility of orienting the individual lenses 9 of the lens arrangement 10 with their optical axes such that the focuses of the converging individual beams form an overall focus which optimally illuminates the viewing field or surgical field.

The LEDs are operated from a power supply unit 13 with a housing 14 having small dimensions so that it can be comfortably held in a pocket, for example in the breast pocket of work clothing, a shirt or a blouse. The housing 14 contains at least one battery pack or battery 15, for example a replaceable battery or a rechargeable battery. Furthermore, in the housing there is control and monitoring electronics 16 monitoring the state of the battery 15 and displays the state or drain of the battery 15 by means of a LED display 16 on the top of the housing 14.

On the top of the housing 14 there are various terminals. In the embodiment shown a terminal 18 for a thin, very flexible cable 19 via which the illumination means 6 is connected to the power supply unit 13, and a terminal 20 for connection of a control line 21 connecting the power supply unit 13 or its electronics 16 to an actuating element 22, for example, to a momentary contact control switch, via which the illumination means 6 can be turned on and off by touch when the power supply unit 13 is turned on.

The actuating element 22 is made such that it can be comfortably attached for example by means of a clip (not shown) or in some other suitable way to the desired location on the clothing of the user of the magnifying glass 1 such that this actuating element 22 can then be actuated by being touched for example with the arm, wrist, elbow, etc. It is possible to turn the illumination means 6 on and off without using the hand; this is very important especially in surgical applications with respect to the hygiene and sterility to be maintained.

On the top of the housing 14 there is a central switch 23 with which the power supply unit overall can be turned on and off. The weight of the illumination means 6 is for example 6 grams. With conventional batteries 15 a long operating life, for example at least 40 hours, can be reached until it is necessary to replace the battery.

The illumination means 6 is not only small and light, but this illumination means and the pertinent power supply unit 13 are also invulnerable to impacts. The size of the housing 14 corresponds for example to the size of a pack of cigarettes or half a pack of cigarettes.

Because it is also possible to use replaceable batteries, i.e. those which cannot be recharged or regenerated, the invention can be used wherever battery chargers are not available or their use is not feasible.

It was assumed above that the lens arrangement 10 is formed by three discrete lenses 9. But of course it is also possible to use, instead of individual lenses, a multiple lens in which the individual lenses are combined into a monolithic multiple lens. Furthermore, it is also possible to use a lens common to all the LEDS instead of several individual lenses or lens elements. In the embodiment shown the lenses 9 are shown as optical convergent lenses. Of course, other focusing elements are conceivable as individual lenses or lens arrangements.

FIG. 5 shows as another possible embodiment, in a partial representation, a board 11 on an illumination means 6a. In this illumination means, LEDs in the form of SMDs are used which enable a very dense arrangement on the board 11 so that in this version the individual light beams of a plurality of these LEDs 12a can be optimally focused by means of a single optical focusing element at the focus of the common light beam 7. As shown in FIG. 5, in this version the LEDs 12a are arranged in several rows and columns so that the LEDs with their light-emitting active layer lie a quadratic grid so that illumination of the working area or viewing area as uniform as possible in all directions takes place.

LEDs 12 or 12a with the illumination means 6 turned on are operated continuously. However, there is also the possibility of operating the LEDs 12 or 12a pulsed, for example with a frequency of 100 Hz. By changing the pulse width control of the light intensity is possible.

Figure 6:
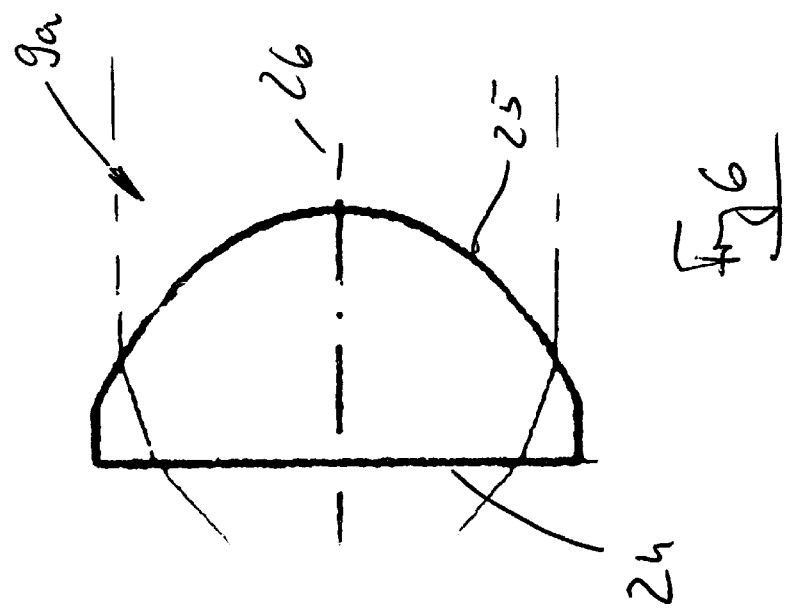
FIG. 6 shows in an individual representation and in a section a focusing lens for use in the illumination means.
Figure 4:
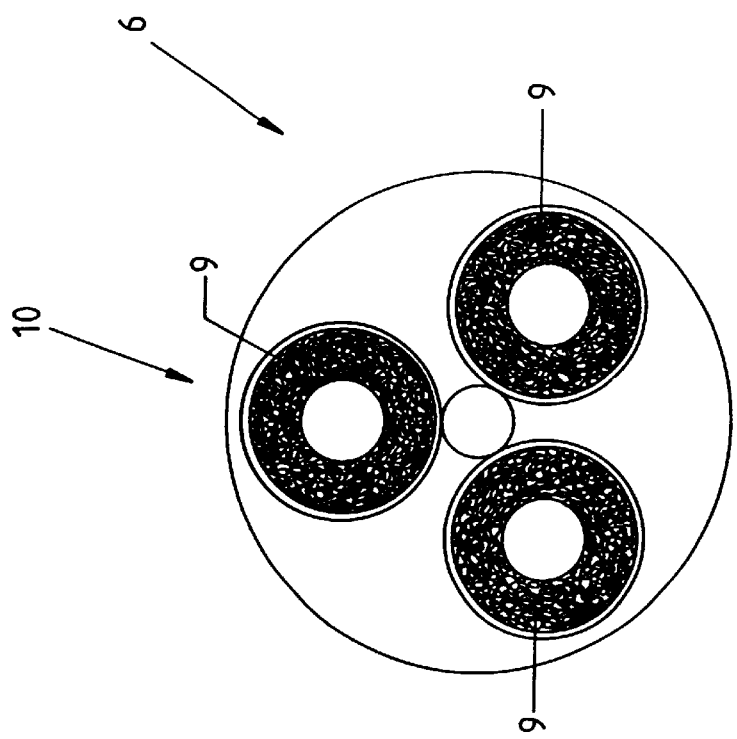
FIG. 4 shows the illumination means of FIG. 3 in a front view.

FIG. 6 shows, in a simplified representation and in a section, another possible version of the focusing lens 9a which is used instead of the focusing lens 9. The focusing lens 9a is an aspherical lens produced by pressing out of a suitable optical material, for example a plastic material which is suitable for optical lenses. The particular feature of the focusing lens 9a is that it has one flat side 24 and one curved side 25 and is made aspherical on the curved side 25, i.e. with a radius of curvature which is smaller in the area of the optical axis and increases as the distance from the optical axis 26 increases. Using this aspherical focusing lens allows better concentration also of the edge beams 27 and thus improves the light output. This is especially important when using LEDs 12 and 12a as the light source.

The invention was described above using embodiments. It goes without saying that numerous other changes and modifications are possible without departing from the idea underlying the invention. Thus it is also possible for example to use LEDs, instead of the lenses 9 or the lens arrangement 10, which are provided with a built-in optical element which focuses the light beam.

Furthermore it is also possible to use, instead of individual LEDs 12 and 12a, multiple LEDs which have several light-emitting emitters on a semiconductor chip or bar. Here it is then also possible to provide several such chips and combine the individual beams of these chips into a common light beam which illuminates the respective viewing or working area.

Furthermore, it is also possible when using several LEDs or one or more multiple LEDs to combine the light of these light sources via optical elements, for example via lenses or lens optics, via optical fiber optics, etc. in an area to be illuminated or at a common focal point or to concentrate the light via optical elements, for example via the aforementioned optical elements or optical fibers at the focal point of common focusing optics or a lens so that then only a single optical focusing or projection system is necessary in spite of a plurality of LEDs.

The illumination means 6 or 6a was described above in conjunction with the magnifying glass 1. However, the illumination means is also suitable for other purposes where it is a matter of illuminating smaller areas, for example as the illumination means in a microscope.

REFERENCE NUMBER LIST 1 magnifying glass
2 optics
3 adapter
4 spectacles
5 headband
6, 6a illumination means
7 light beam
8 housing
9, 9a lens
10 lens arrangement
11, 11a board
12, 12a LED
13 power supply unit 14 housing
15 battery
16 control and monitoring electronics
17 LED display
18 terminal
19 cable
20 control terminal
21 control cable
22 actuating element
23 switch

What is claimed is:

1. A magnifying glass for use in medicine, comprising
   an adjustable adapter attachable to a carrier element;
   a first magnifying optic on said adapter;
   a second magnifying optic on said adapter;
   at least one illumination means on said adapter between said first magnifying optic and said second magnifying optic;
   said illumination means having an electrically operated light source;
   at least one optical focusing element for focusing light from said light source at a focus; and
   a portable power supply unit.

2. The magnifying glass of claim 1, wherein said light source is formed by a plurality of LEDs, said LEDs being spatially offset against one another.

3. The magnifying glass of claim 2, wherein said portable power supply unit comprises at least one battery for operation of said LEDs, said at least one battery located spatially from send light source and connected to said light source via a power supply cable.

4. The magnifying glass of claim 3, wherein at least one of the LEDs forming the light source has a light intensity of at least 2000 mcd.

5. The magnifying glass as claimed in claim 1, wherein at least one LED used as a light source emits white or approximately light white.

6. The magnifying glass as claimed in claim 1, wherein at least one LED forming the light source has a light intensity of at least 3000 mcd.

7. The magnifying glass as claimed in claim 1, wherein the light source is formed by at least one multiple LED having at least two light-emitting areas on a common semiconductor chip or bar.

8. The magnifying glass as claimed in claim 1, wherein the light source is adjustably attached to the optics of the magnifying glass or on the adapter there.

9. The magnifying glass as claimed in claim 1, characterized by a lens arrangement comprising several focusing lenses or is made monolithic with several lens elements or areas acting as focusing lenses.

10. The magnifying glass as claimed in claim 1, characterized by an actuating element arranged separately from the illumination means and controlling the illumination means by touching and/or proximity.

11. The magnifying glass as claimed in claim 1, wherein the illumination means has several LEDS, wherein the light of these LEDs is concentrated by optical elements.

12. The magnifying glass as claimed in claim 1, wherein aspherical lenses focus the light beams of the LEDs.

13. An illumination means for use in medicine or for microscopy, comprising at least one electrically operated light source, wherein the light source is formed by several LEDs spatially offset against one another, and between a first magnifying optic and a second magnifying optic wherein for each LED or each group of several LEDs there is an optical focusing element focusing the light beams of the LEDs at a focus, and a portable power supply unit with at least one battery for operation of the LEDs located spatially separate from the light source and connected to it via a power supply cable.

14. The illumination means as claimed in claim 13, wherein at least one LED used as a light source emits white or approximately light white.

15. The illumination means as claimed in claim 13, wherein at least one LED forming the light source has a light intensity of at least 2000 mcd.

16. The illumination means as claimed in claim 13, wherein the light source is formed by at least one multiple LED having at least two light-emitting areas on a common semiconductor chip or bar.

17. The illumination means as claimed in claim 13, wherein the light source is adjustably attached to the optics of the magnifying glass or on the adapter there.

18. The illumination means as claimed in claim 13, wherein a lens arrangement consists of several focusing lenses or is made monolithic with several lens elements or areas acting as focusing lenses.

19. The illumination means as claimed in claim 13, wherein an actuating element is arranged separately from the illumination means and controls the illumination means by touching and/or proximity.

20. The illumination means as claimed in claim 13, comprising several LEDs or at least one multiple LED with at least two-light emitting areas, and wherein the light of these LEDs or light-emitting areas is concentrated by optical elements.

21. The illumination means as claimed in claim 13, wherein it has several LEDs or at least one multiple LED with at least two-light emitting areas, and wherein the light of these LEDs or light-emitting areas is concentrated by optical elements at the focus of a common lens or in an area to be illuminated.

22. The illumination means as claimed in claim 13, wherein there are aspherical lenses for focusing the light beams of the LEDs.

* * * * *